United States Patent [19]
Giebel et al.

[11] Patent Number: 6,146,363
[45] Date of Patent: Nov. 14, 2000

[54] ANTI-INFECTION CATHETER

[76] Inventors: Marion Giebel, Küderli-Strasse 5/1, 71332 Waiblingen; Willehad Boemke, Düsseldorfer Str. 42, 10707 Berlin, both of Germany; Ülo Palm, 68 Clydesdale Rd., Scotch Plains, N.J. 07076

[21] Appl. No.: 09/299,362

[22] Filed: Apr. 26, 1999

Related U.S. Application Data

[63] Continuation-in-part of application No. PCT/EP96/04618, Oct. 24, 1996.

[51] Int. Cl.$^7$ ...................................................... A61M 5/32
[52] U.S. Cl. ........................................... 604/265; 604/523
[58] Field of Search ..................................... 604/264–265, 604/523, 27, 35, 36, 82–91, 93

[56] References Cited

U.S. PATENT DOCUMENTS 5,433,705  7/1995  Giebel et al. .............................. 604/82

*Primary Examiner*—Corrine McDermott
*Attorney, Agent, or Firm*—Horst M. Kasper

[57] ABSTRACT

An anti-infection catheter arrangement with catheter (1), which exhibits a rigid or flexible catheter tube with the connection piece (10) furnished at a rear side end, wherein the filling and suction device (1) with several reservoirs of active agent is connectable to the connection piece (10), wherein at least one of the active agent reservoirs is filled with a substance, containing at least one antibiotic, or, respectively chemo-therapeutic agent or, respectively, an anti-viral agent, preferably aminoglycoside, preferably gentamicin (13) in an at least minimum effective concentration, wherein a further one of the reservoirs is filled with a substance containing or forming at least one essentially non-damaging material to the tissue cells and blood cells, preferably an anticoagulant, in particular heparin (12), wherein the filling and suction device (1) is constructed such that this substance essentially can be filled into the region of the tip of the catheter tube (15) and wherein the total volume of the reservoirs corresponds at least to the filling volume of the catheter, possibly additionally to the volume of intermediate pieces, in particular of a three-way cock.

22 Claims, 2 Drawing Sheets

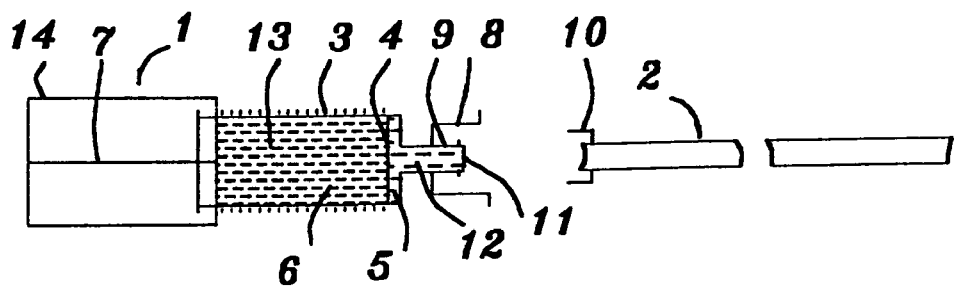
*Fig. 1a*
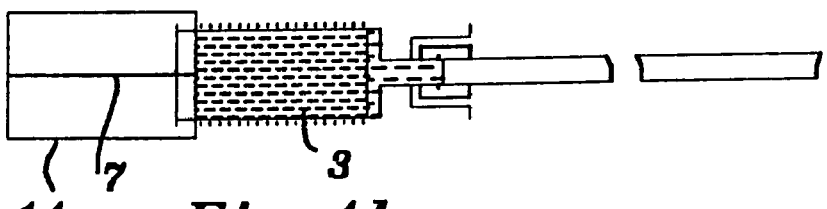
*Fig. 1b*
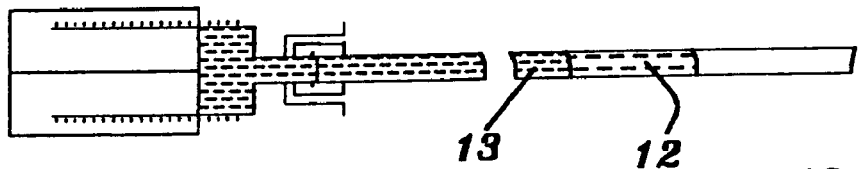
*Fig. 1c*
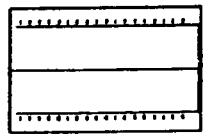
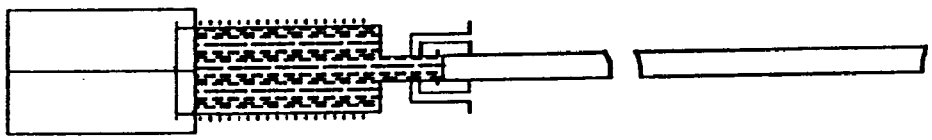
*Fig. 1d*
*Fig. 2a*
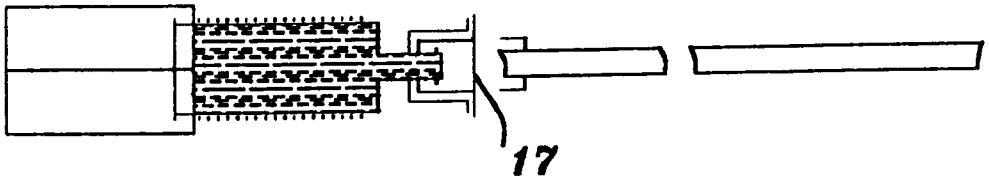
*Fig. 2b*

ANTI-INFECTION CATHETER

CROSS-REFERENCE TO RELATED APPLICATIONS

This application is a continuation-in-part application of another international application filed under the Patent Cooperation Treaty on Oct. 24, 1996, bearing Application No. PCT/EP96/04618, and listing the United States as a designated and/or elected country. The entire disclosure of this latter application, including the drawings thereof, is hereby incorporated in this application as if fully set forth herein.

BACKGROUND OF THE INVENTION

1. Field of the Invention

The present invention relates to an anti-infection catheter and to a method of performing infection preventing catheter injections.

2. Brief Description of the Background of the Invention Including Prior Art

Such a catheter arrangement is known from the printed Patent document WO91/06329. A filling and suction device with at least one active agent reservoir is furnished, wherein the total volume of the active agent reservoir corresponds exactly to the filling volume of the catheter. The volumes have to agree since on the one hand an active agent reservoir volume, which is smaller than the catheter filling volume, can lead to a penetration of active agent into the tip of the catheter and on the other hand an active agent reservoir, which is larger than he filling volume of the catheter, can lead to a penetration of active agent into the blood circulation of the patient and thus lead to a formation of resistance. In addition to the low production tolerances for the volume of the reservoir of active agent of the filling and suction device, the coordination of the filling and suction device to only one type of catheter of a defined filling volume is of disadvantage.

SUMMARY OF THE INVENTION

1. Purposes of the Invention

It is an object of the present invention to furnish a catheter arrangement of the initially recited kind, wherein the catheter caused infection rate is substantially reduced without a danger of a resistance formation even in case of an increased predetermined production tolerance adapted to easy production.

It is an other object of the present invention to furnish a filling and suction device employable for several types of catheter in the context of the large number of types of catheter having similar volumes.

These and other objects and advantages of the present invention will become evident from the description which follows.

2. Brief Description of the Invention

The present invention provides an anti-infection catheter arrangement comprising a catheter exhibiting a rigid or flexible catheter tube having a connection piece disposed at a rear side end. A filling and suction device has a plurality of reservoirs of active agent and is connectable to the connection piece. A first one of the active agent reservoirs is filled with a first substance, containing a member selected from the group consisting of antibiotic, chemo-therapeutic agent, anti-viral agent and mixtures thereof in an at least minimum effective concentration. The anti-viral agent can be an aminoglycoside. A second one of the active agent reservoirs is filled with a second substance containing or forming at least one essentially non-damaging material to the tissue cells and blood cells. The non-damaging material to the tissue cells and blood cells can be an anticoagulant. The filling and suction device is constructed such that the second substance essentially can be filled into the region of the tip of the catheter tube, and the total volume of the reservoirs corresponds at least to the filling volume of the catheter. The total volume of the reservoirs can correspond at least to the filling volume of the catheter plus the volume of intermediate pieces. Alternatively, the total volume of the reservoirs corresponds at least to the filling volume of the catheter plus the volume of a three-way cock.

According to a preferred embodiment, the first reservoir is separated from the catheter tube by a first breakable elastic wall and the second reservoir is separated from the first reservoir by a second breakable elastic wall. The second reservoir is formed by an interior of a cylinder and a piston is furnished for sliding in the second reservoir and capable of breaking the first breakable elastic wall and the second breakable elastic wall upon advancing into the interior of the cylinder.

The filling and suction device to be connectable to the rear side of the catheter is constructed according to the present invention such that the volume of the catheter in the region of the catheter tube tip can be filled with an active agent not damaging to the tissue cells and blood cells, while the actual active agent can be filled in on the side of the connection piece, wherein advantageously at least the same volume can be withdrawn again. The filling volume can thereby also surpass the volume of the catheter, since essentially only substances non-damaging to the tissue can be pressed into the blood path. It is important that the active agent operates only within the catheter and cannot pass into the body of the patient. This assures that the highest possible concentration of active agent can be employed while avoiding the otherwise occurring side effects and resistance developments.

In order to realize the layering of the at least two substances along the catheter tube column, a multi-chamber system of the kind known from the above recited printed Patent document WO91/06329 is suitable. The subject matter known from this printed Patent document WO91/06329 of the claims 2 through 5 relative to the kind of the active agent and of the claims 6 to 8 as well as 10 through 25 relative to the filling and suction device are expressly claimed as advantageous further embodiments of the presented disclosure. Only claim 9 of the printed Patent document WO91/06329 is to be modified in the direction, that the first reservoir on the side of the catheter contains the substantially tissue non-damaging agent, preferably anticoagulant, in particular heparin, and that the second reservoir contains the active agent.

The novel features which are considered as characteristic for the invention are set forth in the appended claims. The invention itself, however, both as to its construction and its method of operation, together with additional objects and advantages thereof, will be best understood from the following description of specific embodiments when read in connection with the accompanying drawing.

BRIEF DESCRIPTION OF THE DRAWING

In the accompanying drawing, in which are shown several of the various possible embodiments of the present invention:

FIG. 1a is a schematic view of an initial application phase of the catheter arrangement according to the present invention during the filling process, where the catheter and the cylindrical casing are disjoint, FIG. 1b is a schematic view of a second application phase of the catheter arrangement according to the present invention during the filling process, where the catheter and the cylindrical casing are joint together, FIG. 1c is a schematic view of a third application phase of the catheter arrangement according to the present invention during the filling process, where the catheter and the cylindrical casing are joint together and a piston has advanced into the cylindrical casing, FIG. 1d is a schematic view of a third application phase of the catheter arrangement according to the present invention during the filling process, where the catheter and the cylindrical casing are joint together and a piston has reached an end of the cylindrical casing, FIG. 2a is a schematic view of the application phase during the suction process, where the catheter and the cylindrical casing are joint together, FIG. 2b is a schematic view of the application phase during the suction process, where the catheter and the cylindrical casing are disjoint, FIG. 3c is a view of a cross-section of the second embodiment along section line 3a—3a in FIG. 3a.

DESCRIPTION OF INVENTION AND PREFERRED EMBODIMENT

Figure 3A:
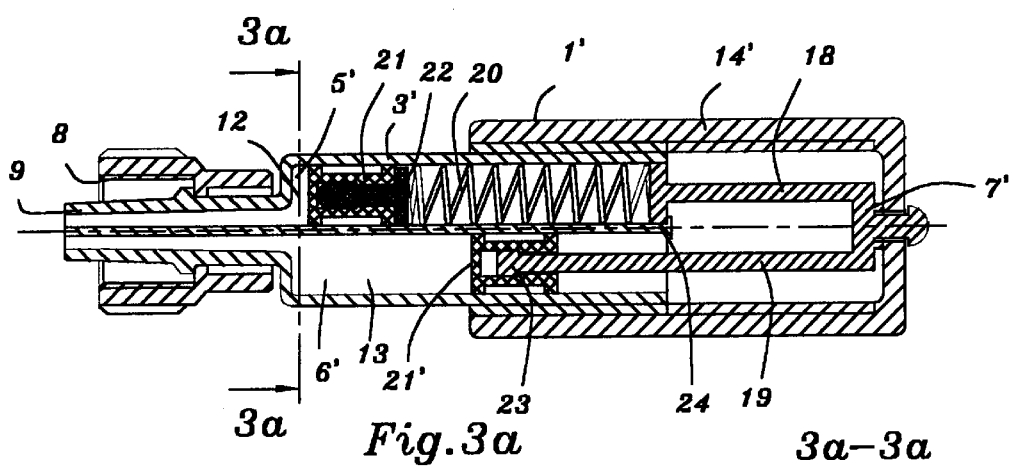
FIG. 3a is a schematic longitudinal sectional view of a second embodiment with the piston in a retracted position.

FIGS. 1a through 2b illustrate the cooperation of a filling and suction device 1 with a catheter 2 according to a first embodiment. The filling and suction device 1 comprises essentially a cylindrical casing 3, a first membrane 4, which subdivides the interior space of the casing into two successive axially disposed chambers 5 and 6 as well as a piston 7, which forms the front side delimitation remote relative to the catheter of the device 1. The device 1 exhibits a Luer-thread 8 and a plug cone 9 for connection to the catheter 2, which are coordinated to a connection piece 10 of the catheter 2. The plug cone 9 is closed at its tip with a second membrane 11. The second chamber 5, delimited by the second membrane 11, the plug cone 9, a part of the cylindrical casing 3 and by the first membrane 4, is filled with heparin 12, while the first chamber 6 delimited by the first membrane 4, a further part of the casing 3 and by the front face of the piston 7 contains an active agent, in particular and antibiotic, for example, gentamicin 13. This two chamber system forms a closed unit, which is present completely sterile in a corresponding packaging unit not illustrated with a protective cap for the second membrane 11, wherein the protective cap is again not illustrated. The protective cap, which is attached to the Luer-thread 8 of the filling and suction device 1, is removed immediately prior to the connection of the catheter 2 in order to avoid as far as possible a contamination, in particular of the second membrane 11, by germs continuously present in the air.

The connection position of the filling and suction device 1 to the catheter 2 is illustrated in FIG. 1b. The piston 7 can be turned in with a screw cap 14 into the cylinder 3. The screw cap 14 can also be furnished as the separate screw cap, whereby a translational motion of the piston is effected.

FIGS. 1c and 1d illustrate the catheter arrangement during and after the filling in of the heparin 12 and of the gentamicin 13 into the catheter 1. The two membranes 4 and 11 have been destroyed by the pressure of the advancing piston from the position shown in FIG. 1b going into the position 1c. The heparin 12 is pressed into the region of the catheter tube tip 15, wherein the filling volume is dimensioned such that no heparin 12 or only a small volume 16 of the heparin 12 can exit from the tip of the catheter tube and pass into the blood path. Toxic reactions are not caused thereby. The heparin 12 counteracts the formation of blood clots, such that blockages of the catheter tube are avoided. In addition the heparin 12 represents a kind of column buffer versus the gentamicin 13, which fills the largest part of the catheter volume. The column buffer shields the gentamicin 13 from the catheterized vessel even then effectively, where the border face between the heparin 12 and the gentamycin 13 becomes blurred in case of a long dwelling time based on mixing processes. Resistance formation by the penetration of even small volumes of gentamicin 13 into the blood are thereby excluded. A single device 1 of a certain size can be employed for several types of catheter depending on the filling volume of the device 1 and the similarity of the volumes of the catheter of different types of catheters.

The solution of antibiotics can be sucked back into the reservoir of the device 1 by screwing back the cap 14. The path of screwing back can be extended somewhat compared to the path of screwing in. Some body liquid from the catheterized vessel, in particular blood, is sucked in thereby beyond the pure filling volume. In this manner it is quasi doubly assured in addition to the operation of the column buffer that no active agent residues remain in the catheter, which residues could be flushed into the body of the patient based on a successive infusion.

The filling and suction device 1 can for example be investigated with respect to its germ content after the suction process. For this purpose of the filling and suction device 1 is closed immediately after the disconnection from the catheter 2, as can be seen in FIG. 2b, with a sterile cap 17.

Figure 3B:
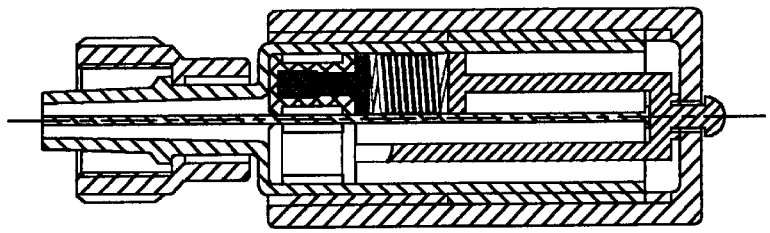
FIG. 3b is a schematic longitudinal sectional view of a second embodiment with the piston in an advanced position.
Figure 3C:
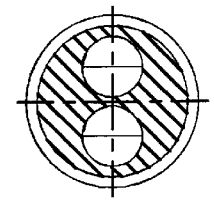

A second embodiment is illustrated in the FIGS. 3a, 3b, and 3c. Here the two chambers 5' and 6' for heparin 12 and gentamicin 13 are disposed not axially successively, but instead side by side as parallel bores of the cylinder 3'. Preferably the bores have substantially the same diameter. A modified piston 7' with two parallel push rods 18 and 19 provides that initially the chamber 5' filled with heparin is emptied and thereafter the chamber 6' filled with gentamicin is emptied. A screw cap 14' is placed on the cylinder 3', which screw cap 14' in operational connection with the piston 7', effects the translational shifting of the piston 7'. The heparin 12 is pressed out of the filling and suction device during a first stroke through the push rod 18 and a connection element of high stiffness, for example, a helical spring 20 and a dog follower 22 furnished with a seal. At the same time the push rod 19 shifts within the similar kind seal 21', whereby however no influence is exerted onto the chamber 6' filled with gentamicin, since this push rod 19 is furnished with a dog follower 23, wherein the dog follower 23 has free play within the seal 21 according to the depth of the column of heparin. Upon continuing the actuation of the screw cap 14' the helical spring 20 is pressed together, while the chamber 6' with the gentamycin 13 is emptied.

The final position after the filling in is shown in FIG. 3b. The two dog followers 22 and 23 act in an opposite direction during the suction process, which is performed by the screwing back of the screw cap 14'. A stop 24 prevents that the piston 7' can be screwed out of the cylinder 3'.

The invention is not limited to the precedingly indicated embodiments. Instead a plurality of variations is conceivable, which use the invention in connection with principally differently fashioned embodiments.

It will be understood that each of the elements described above, or two or more together, may also find a useful application in other types of catheter system configurations and infusion processing procedures differing from the types described above.

While the invention has been illustrated and described as embodied in the context of a anti-infection catheter, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by letters patent is set forth in the appended claims.

What is claimed is:

1. An anti-infection catheter arrangement comprising:
   a catheter exhibiting
   a rigid or flexible catheter tube having a connection piece disposed
   at a rear side end;
   a filling and suction device having a plurality of reservoirs of active agent and connectable to the connection piece,
   wherein one of the active agent reservoirs is filled with a substance, containing a member selected from the group consisting of antibiotic, chemo-therapeutic agent, anti-viral agent and mixtures thereof in an at least minimum effective concentration,
   wherein a second one of the reservoirs is filled with a substance containing or forming at least one essentially non-damaging material to the tissue cells and blood cells,
   wherein the filling and suction device is constructed such that this substance essentially can be filled into the region of the tip of the catheter tube to provide a buffer such that the substance, containing a member selected from the group consisting of antibiotic, chemo-therapeutic agent, anti-viral agent and mixtures thereof does not enter into the blood, and
   wherein the total volume of the reservoirs is larger than the filling volume of the catheter.

2. The anti-infection catheter arrangement according to claim 1 further comprising:
   intermediate pieces, wherein the total volume of the reservoirs corresponds at least to the filling volume of the catheter plus the volume of the intermediate pieces.

3. The anti-infection catheter arrangement according to claim 1 further comprising:
   a three-way cock, wherein the total volume of the reservoirs corresponds at least to the filling volume of the catheter plus the volume of the three-way cock.

4. The anti-infection catheter arrangement according to claim 1, wherein the anti-viral agent is an aminoglycoside.

5. The anti-infection catheter arrangement according to claim 4, wherein the anti-viral agent is gentamicin.

6. The anti-infection catheter arrangement according to claim 1, wherein the non-damaging material to the tissue cells and blood cells is an anticoagulant.

7. The anti-infection catheter arrangement according to claim 6, wherein the non-damaging material to the tissue cells and blood cells is heparin.

8. The anti-infection catheter arrangement according to claim 1, further comprising:
   a three-way cock, wherein the total volume of the reservoirs is larger than the filling volume of the catheter plus the volume of the three-way cock.

9. An anti-infection catheter arrangement comprising:
   a catheter exhibiting
   a rigid or flexible catheter tube having a connection piece disposed
   at a rear side end;
   a filling and suction device having a plurality of reservoirs of active agent and connectable to the connection piece,
   wherein a first one of the active agent reservoirs is filled with a substance, containing a member selected from the group consisting of antibiotic, chemo-therapeutic agent, anti-viral agent and mixtures thereof in an at least minimum effective concentration,
   wherein a second one of the active agent reservoirs is filled with a second substance containing or forming at least one essentially non-damaging material to the tissue cells and blood cells,
   wherein the filling and suction device is constructed such that the second substance essentially can be filled into the region of the tip of the catheter tube to provide a buffer such that the substance, containing a member selected from the group consisting of antibiotic, chemo-therapeutic agent, anti-viral agent and mixtures thereof does not enter into the blood, and
   wherein the total volume of the reservoirs is larger than the filling volume of the catheter.

10. The anti-infection catheter arrangement according to claim 9 wherein the second reservoir is separated from the catheter tube by a first breakable elastic wall;
    wherein the first reservoir is separated from the second reservoir by a second breakable elastic wall;
    wherein the first reservoir is formed by an interior of a cylinder;
    wherein a piston is furnished for sliding in the first reservoir and capable to break the first breakable elastic wall and the second breakable elastic wall upon advancing into the interior of the cylinder.

11. The anti-infection catheter arrangement according to claim 8, wherein the first reservoir is formed by a first bore and wherein the second reservoir is formed by a second bore and wherein the first bore and the second bore are disposed side by side as parallel bores of a cylinder.

12. The anti-infection catheter arrangement according to claim 11, wherein the filling and suction device includes a modified piston with a first push rod and a second push rod disposed in parallel to the first push rod for initially emptying the second reservoir and thereafter emptying the first reservoir.

13. The anti-infection catheter arrangement according to claim 12, further comprising:
    a screw cap placed onto a cylinder surrounding the first reservoir and the second reservoir, wherein the screw cap is operationally connected to the modified piston and effects a translational shifting of the modified piston, wherein a contents of the second reservoir is pressed out of the filling and suction device during a first stroke through the second piston of the modified piston and a connection element of high stiffness; and wherein
    at the same time the first push rod of the modified piston shifts within a seal, wherein however initially no influence is exerted onto the first reservoir, since this first push rod is furnished with a first dog follower, wherein the first dog follower has free play within the seal according to a depth of a column of the contents of the second reservoir and wherein upon continuing the actuation of the screw cap the connection element of high stiffness is pressed together, while the first reservoir is emptied.

14. The anti-infection catheter arrangement according to claim 13, further comprising:

a second dog follower furnished to the second push rod, wherein the first dog follower and the second dog follower act in an opposite direction during a suction process, which suction process is performed by a screwing back of the screw cap; and a stop associated with the second reservoir for preventing the second piston from being screwed out of the second reservoir.

15. The anti-infection catheter arrangement according to claim 13, wherein the connection element of high stiffness is a helical spring and a second dog follower furnished with a seal.

16. The anti-infection catheter arrangement according to claim 11, wherein the first bore and the second bore have substantially the same diameter.

17. An anti-infection catheter arrangement with a catheter (1), which catheter exhibits a rigid or flexible catheter tube with a connection piece (10) furnished at the rear side end, wherein a filling and suction device (1) with two reservoirs of active agent can be attached to the connection piece (10), wherein one of the reservoirs of the agent is filled with a substance, containing at least one antibiotic agent or, respectively, a chemo-therapeutic agent, preferably aminoglycoside, preferably gentamicin (13) in an at least minimum effective concentration, wherein a second one of the two reservoirs is filled with a second substance, containing or forming at least an agent substantially not damaging tissue cells and blood cells, preferably an anticoagulant, in particular heparin (12), wherein the filling and suction device (1) is constructed such that this second substance can be filled essentially into the region of the tip of the catheter tube (15) to provide a buffer such that the substance, containing at least one antibiotic agent or, respectively, a chemo-therapeutic agent, preferably aminoglycoside, preferably gentamicin (13) in an at least minimum effective concentration does not enter into the blood and wherein the total volume of the reservoirs is larger than the catheter filling volume.

18. The anti-infection catheter arrangement according to claim 17, further comprising:

intermediate pieces, wherein the total volume of the two reservoirs is larger than the filling volume of the catheter plus the volume of the intermediate pieces.

19. An anti-infection catheter arrangement comprising:

a catheter tube having a connection piece disposed at a rear side end of the catheter tube;

a filling and suction device having a first reservoir filled with a first agent containing a member selected from the group consisting of antibiotic, chemo-therapeutic agent, anti-viral agent and mixtures thereof in an at least minimum effective concentration;

a first membrane fixedly disposed in the filling and suction device and closing the first reservoir and separating a connection from the first reservoir to the connection piece;

a second reservoir filled with a second agent containing or forming at least one essentially non-damaging material to the tissue cells and blood cells;

a second membrane closing the second reservoir and separating a direct connection from the second reservoir to the connection piece;

a push rod determining the boundaries of the first reservoir and capable of pressing open the first membrane and capable of pressing open the second membrane such that initially the second agent enters into the catheter tube and only thereafter the first agent enters into the catheter tube.

20. The anti-infection catheter arrangement according to claim 19, wherein the second agent essentially is filled first into the region of the tip of the catheter tube to provide a buffer such that the first agent containing a member selected from the group consisting of antibiotic, chemo-therapeutic agent, anti-viral agent and mixtures thereof does not enter into the blood wherein the total volume of the first reservoir and of the second reservoir is larger than the filling volume of the catheter.

21. The anti-infection catheter arrangement according to claim 19, further comprising:

a cylindrical casing surrounding the first reservoir and the second reservoir;

a plug cone attached to the casing and supporting the second membrane;

a Luer thread attached to the plug cone.

22. The anti-infection catheter arrangement according to claim 21 wherein the first reservoir is delimited by the first membrane, a first part of the cylindrical casing and by a front face of a piston attached to the push rod and contains an antibiotic;

wherein the second reservoir is delimited by the second membrane, the plug cone, a second part of the cylindrical casing and by the first membrane and is filled with heparin;

wherein a system of the first reservoir and of the second reservoir forms a closed unit, which is present completely sterile.

* * * * *